US010661089B2

(12) United States Patent
Viavattine

(10) Patent No.: US 10,661,089 B2
(45) Date of Patent: May 26, 2020

(54) ELECTROCHEMICAL CELL WITH ADJACENT CATHODES

(71) Applicant: Medtronic, Inc., Minneapolis, MN (US)

(72) Inventor: Joseph J. Viavattine, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 628 days.

(21) Appl. No.: 15/041,269

(22) Filed: Feb. 11, 2016

(65) Prior Publication Data

US 2016/0158556 A1    Jun. 9, 2016

Related U.S. Application Data

(63) Continuation of application No. 13/674,148, filed on Nov. 12, 2012, now Pat. No. 9,289,611, and a continuation-in-part of application No. 13/302,903, filed on Nov. 22, 2011.

(51) Int. Cl.
| | |
|---|---|
| *A61N 1/378* | (2006.01) |
| *A61N 1/362* | (2006.01) |
| *H01M 6/46* | (2006.01) |
| *H01M 4/64* | (2006.01) |
| *H01M 4/04* | (2006.01) |
| *A61N 1/02* | (2006.01) |
| *H01M 4/02* | (2006.01) |
| *H01M 10/04* | (2006.01) |
| *H01M 6/16* | (2006.01) |
| *H01M 2/02* | (2006.01) |
| *H01M 2/26* | (2006.01) |
| *H01M 10/0525* | (2010.01) |
| *H01M 10/052* | (2010.01) |
| *H01M 10/0583* | (2010.01) |

(52) U.S. Cl.
CPC .............. *A61N 1/378* (2013.01); *A61N 1/02* (2013.01); *A61N 1/362* (2013.01); *H01M 2/0202* (2013.01); *H01M 2/263* (2013.01); *H01M 4/02* (2013.01); *H01M 4/04* (2013.01); *H01M 4/64* (2013.01); *H01M 6/16* (2013.01); *H01M 6/46* (2013.01); *H01M 10/049* (2013.01); *H01M 10/0436* (2013.01); *H01M 10/0472* (2013.01); *H01M 10/0525* (2013.01); *H01M 10/0454* (2013.01); *H01M 10/052* (2013.01); *H01M 10/0583* (2013.01); *H01M 2004/021* (2013.01); *H01M 2220/30* (2013.01); *Y10T 29/49108* (2015.01)

(58) Field of Classification Search
CPC .............. H01M 2/263; H01M 2/0202; H01M 10/0472; H01M 10/0436
See application file for complete search history.

(56) References Cited

U.S. PATENT DOCUMENTS

| | | | |
|---|---|---|---|
| 4,204,036 A | 5/1980 | Cohen et al. | |
| 5,468,569 A * | 11/1995 | Pyszczek | H01M 4/04 29/623.5 |
| 6,265,100 B1 | 7/2001 | Saaski et al. | |
| 6,607,861 B2 | 8/2003 | Gan et al. | |
| 6,617,074 B1 | 9/2003 | Watarai et al. | |
| 6,632,554 B2 | 10/2003 | Doshi et al. | |
| 6,679,926 B1 | 1/2004 | Kajiura et al. | |
| 6,699,265 B1 | 3/2004 | O'Phelan et al. | |
| 7,018,743 B2 | 3/2006 | Guidi et al. | |
| 7,035,078 B1 | 4/2006 | Viavattine | |
| 7,135,250 B2 | 11/2006 | Sasaki et al. | |
| 7,531,274 B1 | 5/2009 | Roy et al. | |
| 7,858,261 B2 | 12/2010 | Schaevitz et al. | |
| 7,927,742 B2 | 4/2011 | Scott et al. | |
| 7,931,987 B2 | 4/2011 | Howard et al. | |
| 8,741,469 B2 | 6/2014 | Ahn et al. | |
| 9,289,611 B2 | 3/2016 | Viavattine | |
| 2004/0127952 A1 | 7/2004 | O'Phelan et al. | |
| 2004/0147961 A1 | 7/2004 | O'Phelan et al. | |
| 2006/0166078 A1 * | 7/2006 | Chen | H01M 2/1653 429/62 |
| 2009/0029259 A1 | 1/2009 | Okazaki et al. | |
| 2009/0136834 A1 * | 5/2009 | Coowar | H01M 2/0267 429/127 |

FOREIGN PATENT DOCUMENTS

| | | |
|---|---|---|
| JP | 2002042855 | 2/2002 |
| WO | 1997/08769 | 3/1997 |

OTHER PUBLICATIONS (PCT/US2012/064615) Annex to Form PCT/ISA/206 Communication Relating to the Results of the Partial International Search, 2 pages, dated Jun. 10, 2013.

* cited by examiner

*Primary Examiner* — Ladan Mohaddes

(57) ABSTRACT

The disclosure includes an electrochemical cell comprising a first cathode and a second cathodes are adjacent one another in a stacked arrangement to form a cathode stack in the electrochemical cell. The first cathode includes a first current collector and a first cathode form of active material covering the first current collector, and the second cathode includes a second current collector and a second cathode form of active material covering the second current collector. The second current collector is in electrical contact with the first current collector. The electrochemical cell further comprises an anode adjacent to the cathode stack, and a separator located between the cathode stack and the anode.

20 Claims, 12 Drawing Sheets

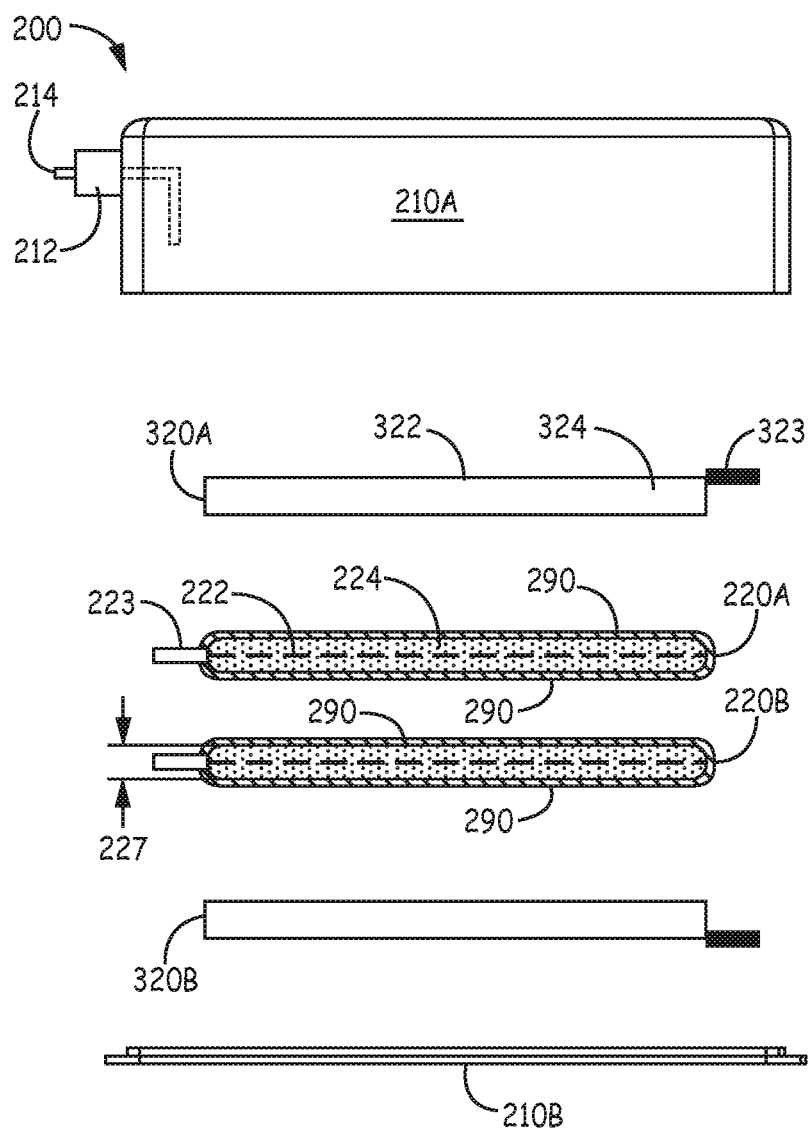
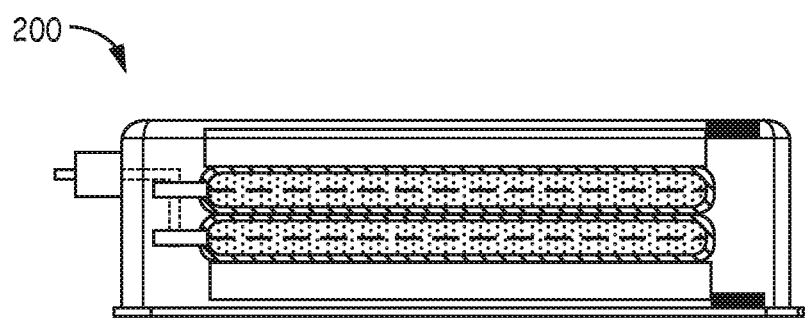
FIG. 3A
FIG. 3B

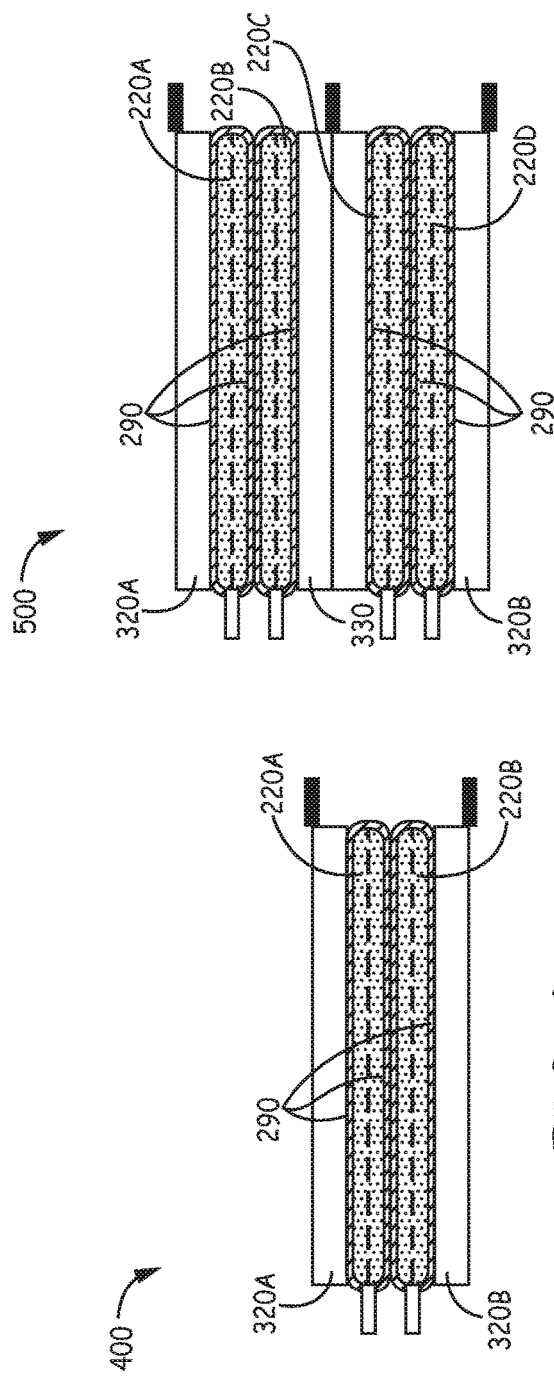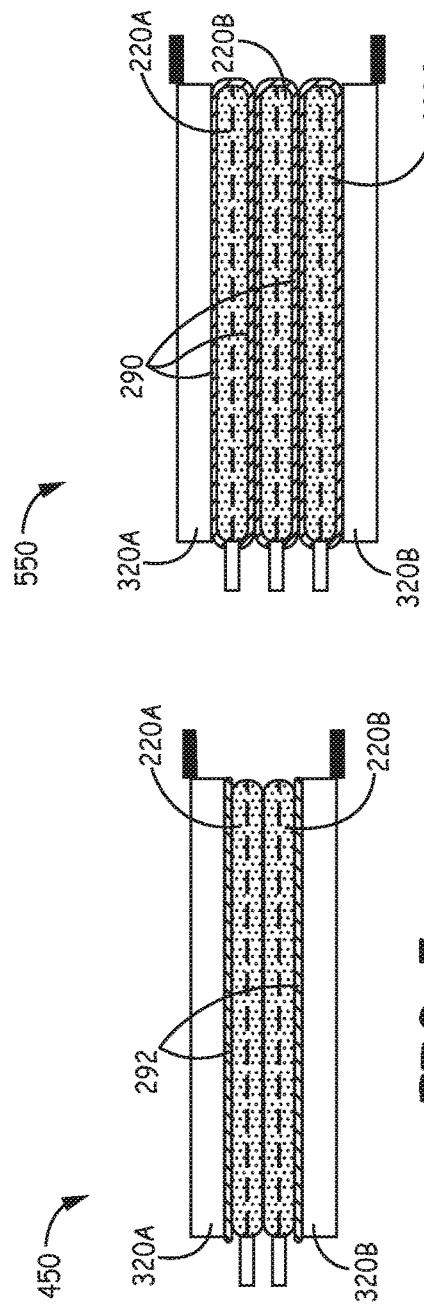

ELECTROCHEMICAL CELL WITH ADJACENT CATHODES

RELATED APPLICATIONS

This application is a continuation of U.S. application Ser. No. 13/674,148, filed Nov. 12, 2012 which is a continuation-in-part of U.S. application Ser. No. 13/302,903, filed Nov. 22, 2011.

FIELD

The invention generally relates to electrochemical batteries, and more particularly, but without limitation, to batteries for implantable medical devices (IMDs).

BACKGROUND

Implantable medical devices (IMDs) may perform a variety of functions, including patient monitoring and therapy delivery. In general, it is desirable to design an IMD to be as small as possible, e.g., in terms of volume, footprint, and/or thickness, while still effectively performing its intended function. For example, decreasing the size of an IMD can increase the number of possible locations in which the IMD can be practically implanted. In addition, a smaller IMD can limit the extensiveness of surgery, reduce the likelihood of infection or rejection of the implant, and improve the comfort, and in some cases cosmetic appearance, of a patient after implantation. In other words, a smaller IMD may be more clinically acceptable than a larger IMD.

Examples of IMDs include implantable stimulators, implantable pulse generators (IPGs) and implantable cardioverter-defibrillators (ICDs). IPGs and ICDs comprise, among other things, a control module, a capacitor, and a battery that are housed in a hermetically sealed container. IMD batteries may include includes a case, a liner, an electrode assembly, electrolyte, and at least one feedthrough extending through the case that serves as a battery terminal. The liner insulates the electrode assembly from the case. The electrode assembly includes electrodes, an anode and a cathode, with a separator there between.

SUMMARY

This disclosure includes electrochemical cells such as a battery in an IMD. The battery may include multiple cathodes stacked on top of each other. Providing multiple cathode plates increases the collector interfacial area. This may reduce cathode resistance. In addition, providing multiple cathode plates may also reduce in-plane expansion of the cathode plates during battery discharge. Finally, providing multiple cathode plates allows more shape flexibility in the thickness direction of the battery as the multiple plates may have different profiles.

In one example, this disclosure includes an electrochemical cell comprising a first cathode and a second cathode. The first and second cathodes are adjacent one another in a stacked arrangement to form a cathode stack in the electrochemical cell. The first cathode includes a first current collector and a first cathode form of active material covering the first current collector, and the second cathode includes a second current collector and a second cathode form of active material covering the second current collector. The second current collector is in electrical contact with the first current collector. The electrochemical cell further comprises an anode adjacent to the cathode stack, and a separator located between the cathode stack and the anode.

In another example, this disclosure includes a battery comprising a first cathode. The first cathode includes a first current collector and a first cathode form of active material covering the first current collector. The battery further comprises a second cathode. The second cathode includes a second current collector and a second cathode form of active material covering the second current collector. The second current collector is in electrical contact with the first current collector. The first and second cathodes are adjacent one another in a stacked arrangement to form a cathode stack in the battery. The battery further comprises an anode adjacent to the cathode stack, a separator located between the cathode stack and the anode, electrolyte, and a battery housing that holds the cathode stack, the anode, the separator, and the electrolyte.

In another example, this disclosure includes a method of manufacture comprising positioning a first cathode and a second cathode adjacent one another in a stacked arrangement to form a cathode stack. The first cathode includes a first current collector and a first cathode form of active material covering the first current collector. The second cathode includes a second current collector and a second cathode form of active material covering the second current collector. The method further comprises positioning an anode adjacent to the cathode stack with a separator located between the cathode stack and the anode, and electrically connecting the first current collector and the second current collector.

The details of one or more examples of this disclosure are set forth in the accompanying drawings and the description below. Other features, objects, and advantages will be apparent from the description and drawings, and from the claims.

BRIEF DESCRIPTION OF DRAWINGS

FIGS. 3A-3B illustrate one example of a battery including an electrochemical cell with adjacent cathodes.

FIGS. 4-9 illustrate examples of electrochemical cells with adjacent cathodes.

DETAILED DESCRIPTION

Implantable medical devices (IMDs) are used to deliver therapy to patients suffering from a variety of conditions. Examples of IMDs include implantable pacemakers and implantable cardioverter-defibrillators (ICDs), which are electronic medical devices that monitor the electrical activity of the heart and provide electrical stimulation to one or more of the heart chambers as needed. For example, a pacemaker senses an arrhythmia, i.e., a disturbance in heart rhythm, and provides appropriate electrical stimulation pulses, at a controlled rate, to selected chambers of the heart in order to correct the arrhythmia and restore the proper heart rhythm. The types of arrhythmias that may be detected and corrected by pacemakers include bradycardias, which are unusually slow heart rates, and certain tachycardias, which are unusually fast heart rates.

ICDs also detect arrhythmias and provide appropriate electrical stimulation pulses to selected chambers of the heart to correct an abnormal heart rate or rhythm. In contrast to pacemakers, however, an ICD can deliver cardioversion and high energy defibrillation pulses that are much stronger than typical pacing pulses. This is because ICDs are generally designed to correct fibrillation and tachycardia episodes. To correct such arrhythmias, an ICD delivers a low, moderate, or high-energy therapy.

Pacemakers and ICDs may be designed with ergonomic shapes that are relatively compliant with a patient's implant location and tend to minimize patient discomfort. For example, corners and edges of the devices may have relatively generous radii to provide a device with smoothly contoured exterior surfaces.

The electrical energy for the therapy delivered by an ICD is generated by delivering electrical current from a power source (battery) to charge capacitors to store energy. The capacitors are capable of rapidly discharging, under control of a processing element, to deliver one or more appropriate waveforms that deliver energy via electrodes disposed in communication with a patient's heart. In order to provide timely therapy to the patient after the detection of ventricular fibrillation, for example, it is necessary to charge the capacitors with the required amount of energy as quickly as possible. Thus, the battery in an ICD must have a high rate capability to provide the necessary current to charge the capacitors. In addition, since ICDs are implanted in patients, the battery must be able to accommodate physical constraints on size and shape.

It is also desirable to minimize the volume occupied by the devices. Improving the performance or charge density of batteries for IMDs, including ICD is desirable in that such improvements facilitate reductions in the size of the devices or improvements in the performance of the devices, such as, for example, an increase in battery life.

Figure 1:
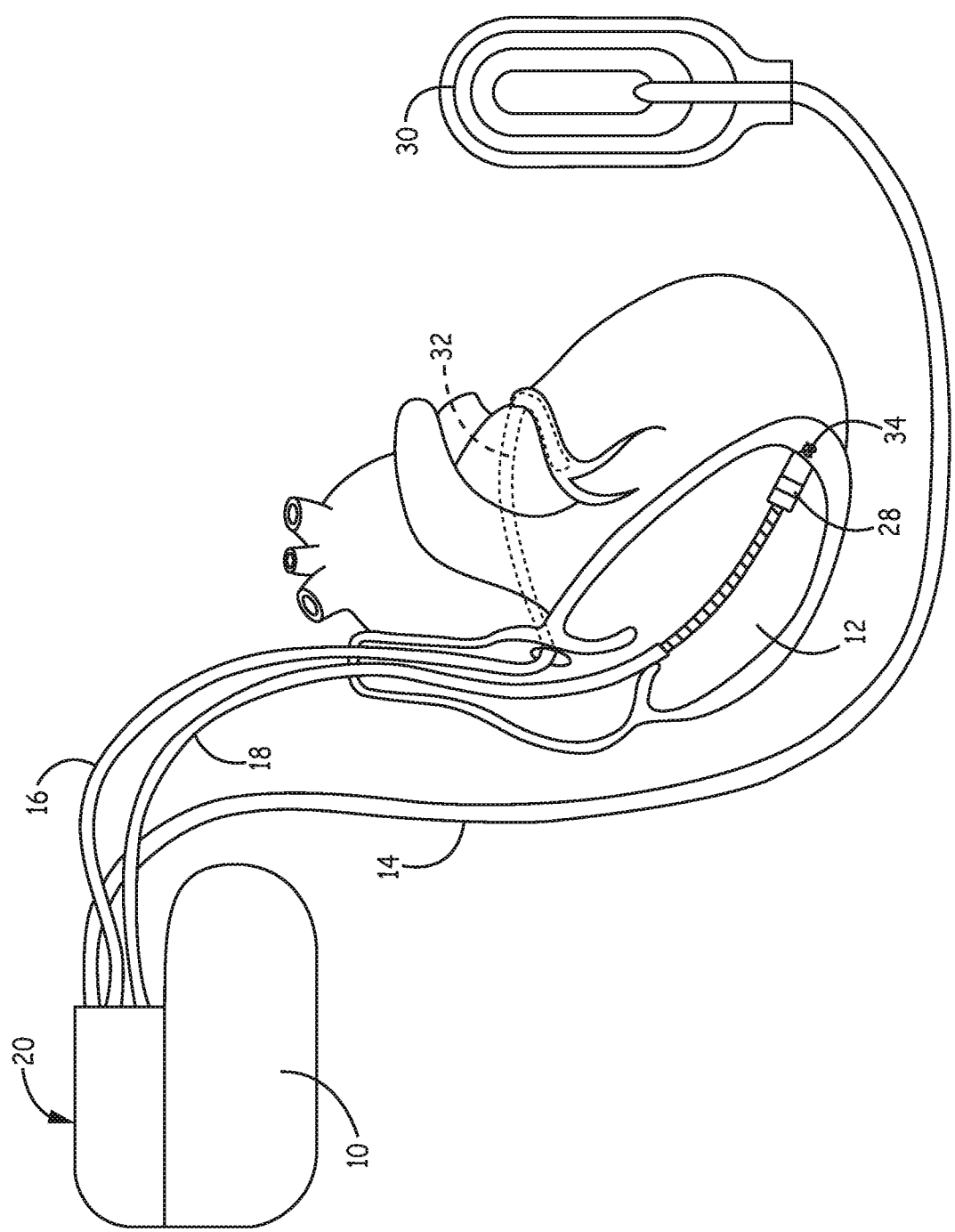
FIG. 1 is a schematic diagram illustrating a pacemaker/cardioverter/defibrillator (PCD) with a battery including an electrochemical cell with adjacent cathodes.

FIG. 1 is a schematic diagram illustrating a pacemaker/cardioverter/defibrillator (PCD) incorporating a battery with at least one electrochemical cell, the electrochemical cell including adjacent cathodes. However, IMD 10 may assume a wide variety of forms. For example, IMD 10 may be an implantable cardiac defibrillator (ICD as is known in the art). Alternatively, or in addition, IMD 10 may be an implantable cardiac pacemaker.

IMD 10 includes associated electrical leads 14, 16 and 18, although it will be appreciated that IMD 10 may include any number of leads suitable for a particular application. Leads 14, 16 and 18 are coupled to IMD 10 by via multi-port connector block 20, which contains separate ports for each of the three leads 14, 16, and 18. Lead 14 is coupled to a subcutaneous electrode 30, which is intended to be mounted subcutaneously in the region of the left chest. Alternatively, or additionally, an active "can" configuration may be employed in which the housing of IMD 10 may serve as an electrode. Lead 16 is a coronary sinus lead employing an elongated coil electrode that is located in the coronary sinus and great vein region of a heart 12. The location of the electrode is illustrated in broken line format at 32, and extends around heart 12 from a point within the opening of the coronary sinus to a point in the vicinity of the left atrial appendage.

Lead 18 may be provided with elongated electrode coil 28, which may be located in the right ventricle of heart 12. Lead 18 may also include a helical stimulation electrode 34, which takes the form of an advanceable helical coil that is screwed into the myocardial tissue of the right ventricle. Lead 18 may also include one or more additional electrodes for near and far-field electrogram sensing.

In the system illustrated, cardiac pacing pulses are delivered between the helical electrode 34 and the elongated electrode coil 28. The electrodes 28 and 34 are also employed to sense electrical signals indicative of ventricular contractions. As illustrated, it is anticipated that the right ventricular electrode 28 will serve as the common electrode during sequential and simultaneous pulse multiple electrode defibrillation regimens. For example, during a simultaneous pulse defibrillation regimen, pulses would simultaneously be delivered between electrode 28 and electrode 30, and between electrode 28 and electrode 32. During sequential pulse defibrillation, it is envisioned that pulses would be delivered sequentially between subcutaneous electrode 30 and electrode 28, and between coronary sinus electrode 32 and right ventricular electrode 28. Single pulse, two electrode defibrillation pulse regimens may also be provided, typically between electrode 28 and coronary sinus electrode 32. Alternatively, single pulses may be delivered between electrodes 28 and 30. The particular interconnection of the electrodes to the IMD 10 will depend somewhat on which specific single electrode pair defibrillation pulse regimen is believed more likely to be employed.

Figure 2:
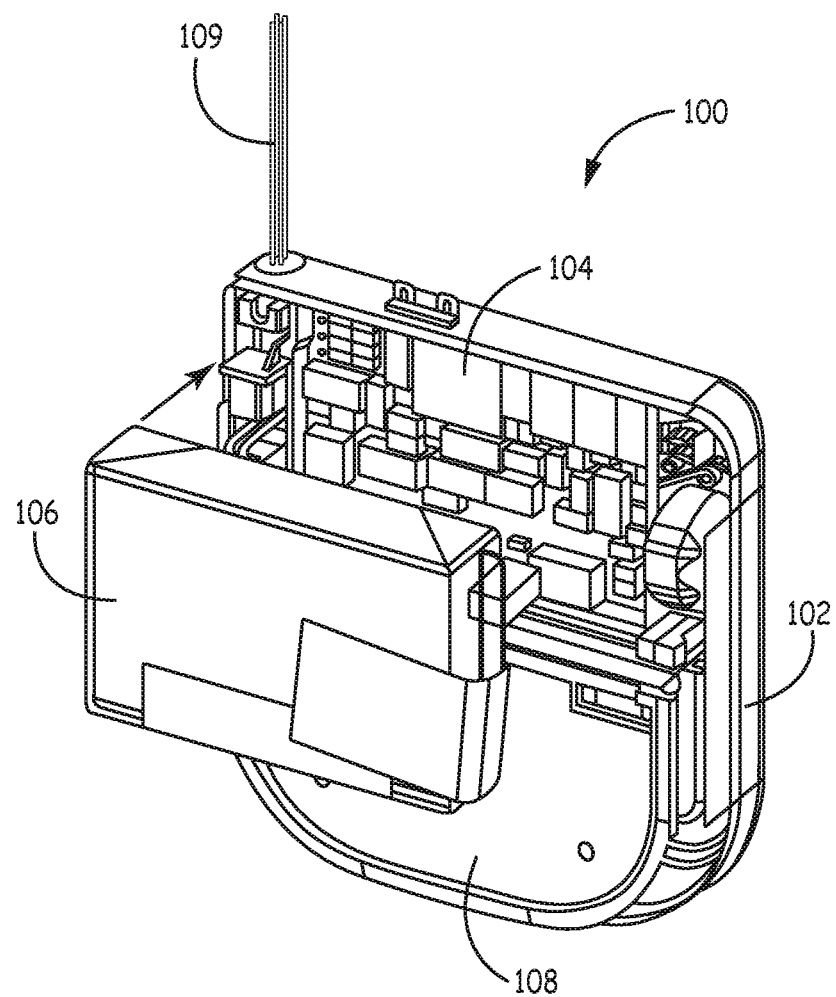
FIG. 2 is a cutaway perspective view of an implantable medical device (IMD) with a battery including an electrochemical cell with adjacent cathodes.

As previously described, IMD 10 may assume a wide variety of forms as are known in the art. One example of various components of an IMD 100 is shown in FIG. 2. More specifically, FIG. 2 depicts an IMD 100, which may be an implantable pulse generator (IPG, e.g., a pacemaker, or an implantable cardioverter-defibrillator (ICD, as examples. IMD 100 includes a case 102, a control module 104, a battery 106 and capacitor(s) 108. Control module 104 controls one or more sensing and/or therapy delivery, such as stimulation therapy functions of IMD 100, which functions may be performed via leads 109. Battery 106 charges capacitor(s) 108 and powers control module 104. Battery 106 includes an electrochemical cell with adjacent cathodes.

FIGS. 3A-3B illustrate battery 200. More specifically, FIG. 3A illustrates an exploded view of the components of battery 200, whereas FIG. 3B shows in the components of battery 200 in a fully-assembled configuration. As one example, battery 200 may be used as battery 106 in IMD 100 (FIG. 2), although battery 200 may also be used in other applications such as other IMDs or other devices that use batteries. In addition, a battery including any of the electrochemical cells disclosed herein, including any of the electrochemical cells disclosed with respect to FIGS. 4-9, 12 and 13 may also be used as battery 106 in IMD 100 (FIG. 2).

Battery 200 includes an electrochemical cell including two anodes 320A, 320B (collectively "anodes 320") and two cathodes 220A, 220B (collectively "cathodes 220"). Battery 200 further includes a two-part housing including cup 210A and cover 210B (collectively housing "210"). Feedthrough 212 includes feedthrough pin 214 that passes through housing 210 and connects to cathodes 220 to provide a positive terminal for battery 200.

Cathodes 220 each include a current collector 222 and a cathode form 224 of active material covering the current collector 222. As one example, current collector 222 may be a metallic screen formed from aluminum, stainless steel, nickel, titanium, copper an alloy thereof or other suitable conductive material. Electrically conductive tab 223 is directly connected to current collector 222 and provides an electrical connection path to current collector 222. In some examples, tab 223 may be a unitary component with current collector 222.

The active material of cathode form 224 may comprise any cathode material known to those in the art. In different examples, the active material of cathode form 224 may include metal oxides (e.g. vanadium oxide, silver vanadium oxide (SVO), manganese dioxide etc.), carbon monofluoride (CFx) and hybrids thereof (e.g., $CF_x+MnO_2$), combination silver vanadium oxide (CSVO), lithium ion, other rechargeable chemistries, or other suitable compounds or any combination thereof. Cathode form 224 may also include binder and other inert ingredients. For example, cathode 220 may be formed by creating a mixture of active material powder, binder powder, solvent and then compressing the mixture over current collector 224 or otherwise coating current collector 224 with the mixture. Other techniques known to those in the art may also be used to from cathode 220.

Anodes 320 each include a current collector 322 and a form 324 of active anode material disposed over the current collector 322. As one example, current collector 322 may be a metallic plate or foil, such as aluminum, stainless steel, nickel, titanium, copper an alloy thereof or other suitable conductive material. Electrically conductive tab 323 is directly connected to current collector 322 and provides an electrical connection path to current collector 322. In some examples, tab 323 may be a unitary component with current collector 322. The active material of anode form 324 may comprise any anode material known to those in the art. In one example, the active material of anode form 324 may comprise graphite, lithium titanate, lithium, a lithium alloy, another active material or a combination thereof. Anode form 324 may also include binder and other inert ingredients. For example, anode 320 may be formed by creating a mixture of active material powder, binder powder, solvent and then compressing the mixture over current collector 322 or otherwise coating current collector 322. Other techniques known to those in the art may also be used to from anode 320.

Cathodes 220A, 220B are positioned adjacent one another in a stacked arrangement to form a cathode stack in the electrochemical cell of battery 200. Anodes 320 are positioned on opposite sides of the cathode stack. Locating cathodes 220A, 220B in a stacked arrangement within battery 200 may provide one or more advantages when compared to a battery in which does not includes multiple cathodes or in which the cathodes are not located adjacent to each other. As one example, placing anodes on both sides of a cathode stack increases the area of the anode-cathode interface of the battery, thereby lowering the resistance of the battery.

As another example, during discharge of a battery, such as battery 200, the cathodes may expand in a direction about perpendicular to the thickness dimension of the cathode. For reference, the thickness of cathode 220B is indicated in FIG. 3A with reference number 227. The amount of expansion is dependent on the thickness of the cathode, e.g., thickness 227 of cathode 220B. For example, the expansion may be approximately equal to the thickness of the cathode. By including multiple cathodes in a cathode stack, as with cathodes 220A, 220B in battery 200, in place of a single, thicker cathode, the cathode stack can be expect to expand less than the single thicker cathode would during discharge of the battery because each cathode in the cathode stack is thinner than the single thicker cathode having the same total charge capacity as the cathode stack would be. Because battery housing designs, such as battery housing 200 should account for cathode expansion during discharge, limiting the expansion of the cathodes in the battery by having a cathode stack instead of a single cathode may allow the cathode stack to more efficiently fill the interior area of the battery housing as compared to a battery within a single cathode. This may increase the charge density of the battery.

In another example, having multiple cathodes in a cathode stack instead of a single cathode may decrease the time need to fill housing 210 with electrolyte during manufacturing of the battery. For example, housing 210 may include one or more fill ports (not shown) used to draw electrolyte, such as an electrolyte including a lithium salt solution, after assembling the electrode stack, but before sealing housing 210. Because multiple cathodes in a cathode stack have a greater surface area than a single cathode having the same charge capacity, the electrolyte may permeate the cathodes in a cathode stack faster than it would permeate the single thicker cathode having the same charge capacity of the cathode stack. For example, if a battery with the single thicker cathode having the same charge capacity of the cathode stack of battery 200 takes two minutes to fill with electrolyte during assembly of the battery, battery 200 may take a minute or less to fill with electrolyte. Also because multiple cathodes in a cathode stack have a greater surface area than the single thicker cathode having the same charge capacity, the electrolyte may more completely permeate the cathodes of the cathode stack.

In battery 200, cathodes 220A, 220B are substantially similar. For example, the active material of cathode 220A is substantially similar to the active material of cathode 220B. In addition, cathode 220A has a substantially similar shape and profile to that of cathode 220B. In addition, cathodes 220A, 220B may be considered interchangeable within battery 200. However, in other examples of a battery having multiple cathodes in a cathode stack, the cathodes of the cathode stack may be different from each other. For example, one or more cathodes in the cathode stack may facilitate a higher power output whereas one or more other cathodes in the cathode stack may provide a higher energy density. As another example, the cathodes may have different shapes facilitate an irregularly shaped battery. This may allow for more efficient packing of components in an electronic device including the battery. This may be particularly advantageous with respect to IMDs where it is generally desirable to design an IMD to be as small as possible, e.g., in terms of volume, footprint, and/or thickness.

Battery 200 further includes separator 290 positioned between cathodes 220 and anodes 320. Separator 290 is a permeable membrane that functions to keep cathodes 220 and anodes 320 physically separated to prevent an electrical short circuit. As one example, separator 290 may be a polymer separator. In the example of battery 200, cathodes 220 are covered by separator layers 290, which may simplify the construction and assembly process of battery 200. In other examples, separator layers 290 may only be placed between adjacent cathodes and anodes.

Feedthrough 212 includes a feedthrough pin 214 that extends through housing 210, and an insulator (not shown) separating feedthrough pin 214 from housing 210. Feedthrough pin 214 directly connects to current collectors 222 of cathodes 220 via electrically conductive tabs 223. For example, electrically conductive tabs 223 may include apertures to receive feedthrough pin 214, and feedthrough pin 214 may be welded to electrically conductive tabs 223. In this manner, feedthrough pin 214 serves as positive terminal for battery 200.

In another example, the cathode stack may include a common current collector element folded into a compact configuration, the common current collector element having a central portion and a plurality of tab portions extending outwardly from the central portion when the common current collector element is unfolded, the tabs each having a generally planar plate portion. Current collectors 222 are included in the tabs of the common current collector element, such that the common current collector element provides a direct electrical connection between each cathode 220. The central portion of the common current collector element being folded in the compact configuration such that the plate portions are positioned to generally overlap each other in the stacked arrangement, and the tab portions being folded in the compact configuration such that the stacked plate portions are spaced apart from each other in the stacked arrangement of cathodes 220 in the cathode stack. For example, techniques relating to foldable common current collector elements are disclosed in U.S. Pat. No. 7,035,078 to Viavattine, titled "FOLDED PLATE ELECTRODE ASSEMBLIES FOR BATTERY CATHODES," the entire content of which is incorporated by reference herein.

Anodes 320 connect directly to housing 210, via anode collectors 322 and/or electrically conductive tabs 323. In this manner, battery 210 represents a case-negative configuration in that housing 210 serves as negative terminal for battery 200. In other examples, a battery including an electrochemical cell in accordance with the techniques disclosed herein may be arranged in a case-positive configuration or a case-neutral configuration. In the example of case neutral, the battery would include a separate positive and negative battery terminals, and may include, for example, two feedthroughs, one serving as a positive terminal and the other serving as a negative terminal for the battery. In any of these examples, the battery may include a liner (not shown) between the electrode stack and the interior of the battery housing to electrically insulate the anodes and cathodes from each other and from the battery housing.

Battery 200 includes one example of an electrochemical cell with adjacent cathodes, but there are many other electrochemical cells configurations including adjacent cathodes in accordance with the techniques disclosed herein. FIGS. 4-9 illustrate some examples of electrochemical cells with adjacent cathodes.

FIG. 4 illustrates electrochemical cell 400. Electrochemical cell 400 is the same as the electrochemical cell of battery 200. Electrochemical cell 400 includes cathodes 220A, 220B, which are positioned adjacent one another in a stacked arrangement to form a cathode stack. Anodes 320 are positioned on opposite sides of the cathode stack. Separator 290 is positioned over cathodes 220, such that separator 290 is positioned not only between cathodes 220 and anodes 320, but also between cathodes 220A, 220B themselves. As previously mentioned, the arrangement of separator 290 and cathodes 220 may simplify assembly of a battery including electrochemical cell 400. For example, separator 290 would not need to be stacked within separately within the battery, and cathodes 220A, 220B may be interchangeable.

In other examples, an electrochemical cell may include separator only between a cathode stack and adjacent anodes. One such example is illustrated as electrochemical cell 450 in FIG. 5. Electrochemical cell 450 includes cathodes 220A, 220B, which are positioned adjacent one another in a stacked arrangement to form a cathode stack. Anodes 320 are positioned on opposite sides of the cathode stack. Separator 292 is positioned only between cathodes 220 and anodes 320, but not between cathodes 220A, 220B themselves. As compared to electrochemical cell 400, electrochemical cell 450 includes two less layers of separator, which reduces the thickness of electrochemical cell 450 without reducing the charge capacity electrochemical cell 450. For this reason, the configuration of electrochemical cell 450 may be expected to provide a higher charge density than the configuration of electrochemical cell 400.

FIG. 6 illustrates electrochemical cell 500, which represents another example of an electrochemical cell with adjacent cathodes. Electrochemical cell 500 includes cathodes 220A, 220B, which are positioned adjacent one another in a stacked arrangement to form a first cathode stack. Electrochemical cell 500 also includes cathodes 220C, 220D, which are positioned adjacent one another in a stacked arrangement to form a second cathode stack. Anode 330 is positioned between the first and second cathode stack, whereas anodes 320A, 320B are positioned adjacent the first cathode stack and the second cathode stack respectively and opposite anode 330. Separator 290 is positioned over cathodes 220, such that separator 290 is positioned not only between cathodes 220 and anodes 320, 330, but also between cathodes 220A, 220B and between 220C, 220D. As previously mentioned, the arrangement of separator 290 and cathodes 220 may simplify assembly of a battery including electrochemical cell 500. For example, separator 290 would not need to be stacked within separately within the battery, and cathodes 220A, 220B, 220C, 220D may be interchangeable.

FIG. 7 illustrates electrochemical cell 550, which represents another example of an electrochemical cell with adjacent cathodes. Electrochemical cell 550 includes cathodes 220A, 220B, 220C that are positioned adjacent one another in a stacked arrangement to form a cathode stack. Anodes 320 are positioned on opposite sides of the cathode stack. Separator 290 is positioned over cathodes 220, such that separator 290 is positioned not only between cathodes 220 and anodes 320, but also between cathodes 220A, 220B, 220C themselves. As previously mentioned, this arrangement may simplify assembly of a battery including electrochemical cell 550. For example, separator 290 would not need to be stacked within separately within the battery, and cathodes 220A, 220B, 220C may be interchangeable.

The electrochemical cells of FIGS. 4-7 each include substantially similar cathodes, i.e., cathodes 220. However, in other examples, in an electrochemical cell including multiple cathodes in a cathode stack, the cathodes of the cathode may not all be substantially similar to each other. For example, one or more cathodes in the cathode stack may facilitate a higher power output whereas one or more other cathodes in the cathode stack may provide a higher energy density. As another example, the cathodes may have different shapes facilitate an irregularly shaped battery. This may allow for more efficient packing of components in an electronic device including the battery. This may be particularly advantageous with respect to IMDs where it is generally desirable to design an IMD to be as small as possible, e.g., in terms of volume, footprint, and/or thickness.

Figure 8:
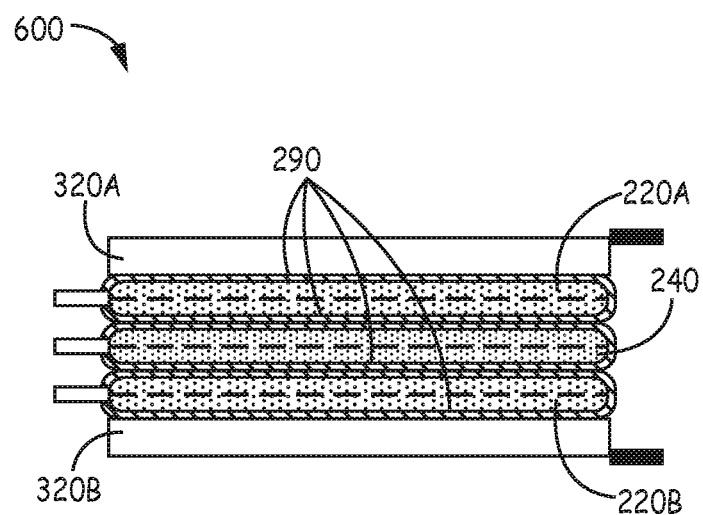

FIG. 8 illustrates electrochemical cell 600, which represents one example configuration in which cathodes in a cathode stack are not substantially similar to one another. Electrochemical cell 600 includes cathodes 220A, 220B, 240, which are positioned adjacent one another in a stacked arrangement to form a cathode stack. Cathodes 220 include a different active material than cathode 240. For example, the active material of cathodes 220 may facilitate a higher power output, whereas the active material of cathode 240 provides a higher energy density. For example, because cathodes 220 are positioned at the anode-cathode interfaces within electrochemical cell 600, the power of electrochemical cell 600 may be increased compared to an electrochemical cell 600 including only multiple cathodes 240. However, because the active material of cathode 240 provides a higher energy density than that of cathodes 220, the energy density of electrochemical cell 600 may be increased compared to an electrochemical cell 600 including only multiple cathodes 220.

Anodes 320 are positioned on opposite sides of the cathode stack of electrochemical cell 600. Separator 290 is positioned over cathodes 220, 240, such that separator 290 is positioned not only between cathodes 220 and anodes 320, but also between cathodes 220A, 220B, 240 themselves. As previously mentioned, this arrangement may simplify assembly of a battery including electrochemical cell 600. For example, separator 290 would not need to be stacked within separately within the battery.

Figure 9:
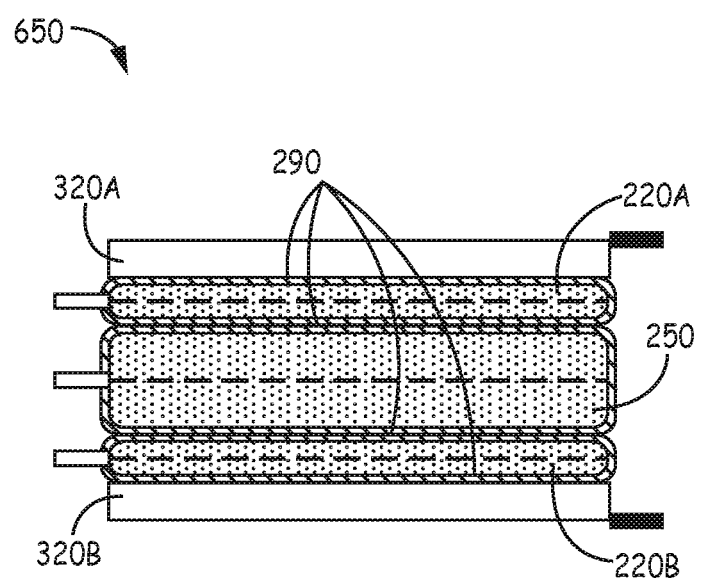

FIG. 9 illustrates electrochemical cell 650, which represents another configuration in which cathodes in a cathode stack are not substantially similar to one another. Electrochemical cell 650 includes cathodes 220A, 220B, 250, which are positioned adjacent one another in a stacked arrangement to form a cathode stack. As shown in FIG. 9, cathode 250 is thicker than cathodes 220. Due to the different thicknesses of cathodes 220, 250, cathodes 220 may facilitate a higher power output, whereas cathode 250 may provide a higher energy density than cathodes 220. For example, the increased thickness of cathode 250 as compared to cathodes 220 allows more active material without any additional current collector material. In this manner, cathode 250 may provide a higher energy density than cathodes 220. However, the greater surface area of cathodes 220 as compared to cathode 250 may allow cathodes 220 to facilitate a higher power output than in a cathode stack having only thicker cathodes.

Anodes 320 are positioned on opposite sides of the cathode stack of electrochemical cell 650. Separator 290 is positioned over cathodes 220, 250, such that separator 290 is positioned not only between cathodes 220 and anodes 320, but also between cathodes 220A, 220B, 250 themselves. As previously mentioned, this arrangement may simplify assembly of a battery including electrochemical cell 650. For example, separator 290 would not need to be stacked within separately within the battery.

While the configurations of the electrochemical cells in FIGS. 4-9 represent some examples of electrochemical cells with adjacent cathodes, these examples are merely for illustrative purposes and numerous other examples exist. For example, the techniques demonstrated with electrochemical cells in FIGS. 4-9, 12 and 13, as well as the battery of FIGS. 10A-10B may be combined in any manner to create different configurations of electrochemical cells with adjacent cathodes.

Figure 10A:
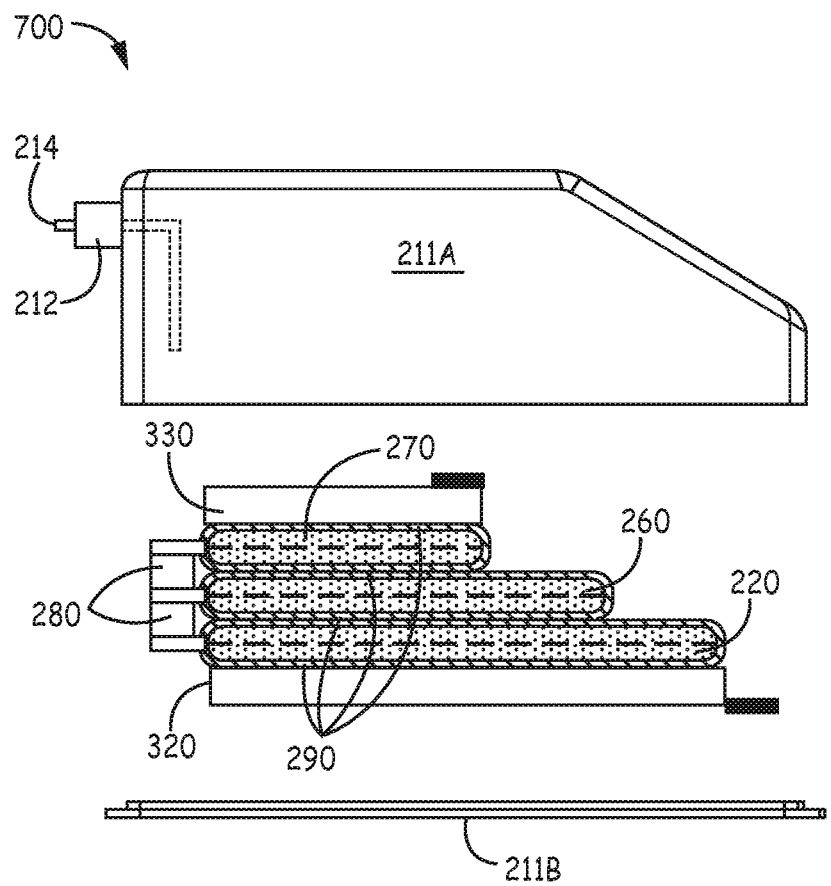
FIGS. 10A-10B illustrate an example battery including an electrochemical cell with adjacent cathodes having different lengths such that the battery has a varying thickness.
Figure 10B:
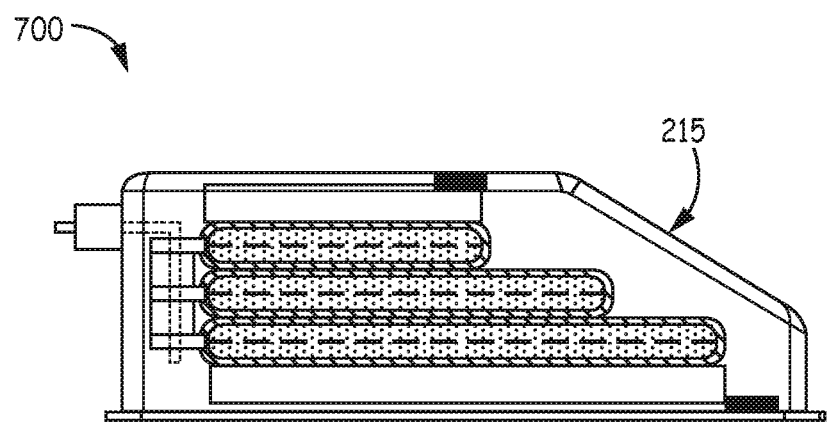

FIGS. 10A-10B illustrate battery 700. More specifically, FIG. 10A illustrates an exploded view of the components of battery 700, whereas FIG. 10B shows in the components of battery 700 in a full-assembled configuration. As one example, battery 700 may be used as battery 106 in IMD (100), although battery 700 may also be used in other applications such as other IMDs or other devices that use batteries. Battery 700 includes an electrochemical cell including two anodes 320, 330 and three cathodes 220, 260, 270. Battery 700 further includes two-part housing including cup 211A and cover 211B (collectively housing "211"). Feedthrough 212 includes feedthrough pin 214 that passes through housing 211 and connects to cathodes 220, 260, 270 to provide a positive terminal for battery 700.

Battery 700 is substantially similar to battery 200 (FIGS. 3A-3B), except that battery 700 includes anodes and cathodes of varying lengths such that battery 700 has a varying thickness. This may allow for more efficient packing of components in an electronic device including battery 700. For example, battery 700 may be designed to fill an irregular available space within an IMD housing or an IMD housing may be designed with a more preferable profile, such as a profile with more rounded corners. Because battery 700 is substantially similar to battery 200, for brevity features of battery 700 that are the same as or substantially similar to features already described with respect to battery 200, are described with limited or no detail with respect to battery 700.

Cathodes 220, 260, 270 each include a current collector and a cathode form of active material covering the current collector. Cathode 260 has a length shorter than cathode 220 and cathode 270 has a length shorter than cathode 260 as measured in a direction about perpendicular to the thickness of the cathode stack. Similarly, anode 330 has a length shorter than anode 320 as measured in a direction about perpendicular to the thickness of the cathode stack. The length of anode 330 corresponds to the length of cathode 270, and the length of anode 320 corresponds to the length of cathode 220. The varying lengths of cathodes 220, 260, 270 and anodes 320, 330 allows battery housing 211 to have angled surface 215, rather than having a rectangular profile as battery housing 210 of battery 200 (FIGS. 3A-3B). Specifically, a thickness of battery housing 211 as measured in the direction about perpendicular to the thickness of the cathode stack varies to conform to the different lengths of anodes 320, 330 and the different lengths of the cathodes 220, 260, 270.

Battery 700 further includes separator 290 positioned between cathodes 220, 260, 270 and anodes 320, 330. Separator 290 is a permeable membrane that functions to keep cathodes 220, 260, 270 and anodes 320, 330 physically separated to prevent an electrical short circuit. As one example, separator 290 may be a polymer separator. In the example of battery 700, cathodes 220, 260, 270 are covered by separator layers 290, which may simplify the construction and assembly process of battery 700. In other examples, separator layers 290 may only be placed between adjacent cathodes and anodes.

Feedthrough 212 includes a feedthrough pin 214 that extends through housing 211, and an insulator (not shown) separating feedthrough pin 214 from housing 211. Feedthrough pin 214 directly connects to the current collectors of cathodes 220, 260, 270 via electrically conductive tabs of the cathodes. For example, the electrically conductive tabs may include apertures to receive feedthrough pin 214, and feedthrough pin 214 may be welded to electrically conductive tabs 223. In this manner, feedthrough pin 214 serves as positive terminal for battery 700. Battery 700 also includes metal spacers 280 between the electrically conductive tabs of the current collectors of cathodes 220, 260, 270. Metal spacers 280 also include apertures to receive feedthrough pin 214. In one example, the electrically conductive tabs of the current collectors of cathodes 220, 260, 270 may be first welded to metal spacers 280, and then the entire cathode stack may be positioned such that and feedthrough pin 214 extends though all of the electrically conductive tabs of the current collectors of cathodes 220, 260, 270 and through metal spacers 280. Then a single weld on the bottom side of the electrically conductive tabs of the current collector of cathode 220 may be used to electrically connect the entire cathode stack to feedthrough pin 214.

Anodes 320 connect directly to housing 211, via anode collectors 322 and/or electrically conductive tabs 323. In this manner, battery 211 represents a case-negative configuration in that housing 211 serves as negative terminal for battery 700. In other examples, a battery including an electrochemical cell in accordance with the techniques disclosed herein may be arranged in a case-positive configuration or a case-neutral configuration.

Figure 11:
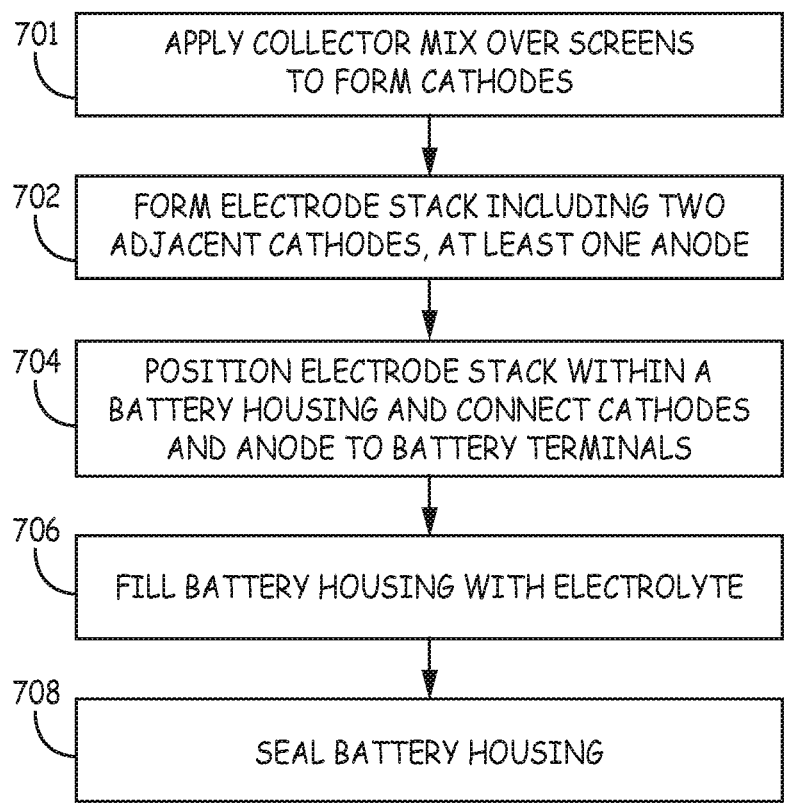
FIG. 11 is a flow chart illustrating techniques for manufacturing a battery including an electrochemical cell with adjacent cathodes.

FIG. 11 is a flow chart illustrating techniques for manufacturing a battery including an electrochemical cell with adjacent cathodes. For clarity, the techniques of FIG. 11 are described with respect to battery 200 (FIG. 3A-3B).

First, cathode 220A and cathode 220B are manufactured with separate cathode forms 224. In some examples, collector mix including an active cathode material is applied to the current collectors 222 to form cathode 220A and cathode 220B (701). Each current collector 222 may be a distinct component or the current collectors may be part of a foldable common current collector element as discussed previously. In some example, current collectors 222 may be coated with the active cathode material to create cathode forms 224. In other examples, the active cathode material may be compressed over current collectors 222 in a mold to create cathode forms 224. Other techniques may also be used to apply active material to current collectors 222. Then, cathode 220A and cathode 220B are positioned adjacent one another in a stacked arrangement to form a cathode stack. As previously mentioned, cathodes 220 each include a current collector 222 and a cathode form 224 of active material covering the current collector 222.

Next, anodes 320 are positioned adjacent to the cathode stack that includes cathodes 220 (702). Separator 290 is located between the cathode stack and anodes 320. The electrode stack, including the cathode stack of cathodes 220 and anodes 320 is placed within battery housing 210. Anode 320A is electrically connected to housing cup 210A, and anode 320B is electrically connected to housing cover 210B such that that housing 210 serves as negative terminal for battery 200. In addition, feedthrough pin 214 of feedthrough 212 directly connects to current collectors 222 of cathodes 220 via electrically conductive tabs 223. For example, electrically conductive tabs 223 may include apertures to receive feedthrough pin 214, and feedthrough pin 214 may be welded to electrically conductive tabs 223. In this manner, feedthrough pin 214 serves as positive terminal for battery 200.

Once the electrode stack is positioned within housing cup 210A, cover 210B is secured to cup 210A and sealed. For example, housing cover 210B may be welded to housing cup 210A. Then housing 210 is filled with electrolyte via fill port on housing 210 (706). In one example, a vacuum may be applied to a vacuum port on housing 210 while filling housing 210 with electrolyte to increase the fill rate of housing 210. Once housing 210 is filled with electrolyte, the fill port and the vacuum port (if any) are sealed (708).

Figure 12:
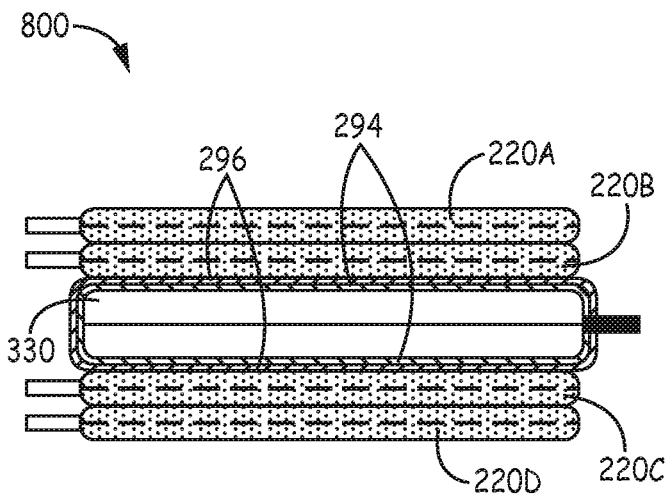
FIGS. 12 and 13 illustrate more examples of electrochemical cells with adjacent cathodes.

In the examples of batteries 200, 700 and electrochemical cells 400, 450, 500, 550, 600, 650, the electrode stacks include anodes outside of the cathode stacks. However, as illustrated in FIGS. 12 and 13, electrochemical cells with adjacent cathodes may also be configured such that cathodes stacks are outside of the anodes.

Electrochemical cell 800 includes cathodes 220A, 220B, 220C, 220D and anode 330. In the example of electrochemical cell 800, illustrated in FIG. 12, a first cathode stack including cathodes 220A, 220B is located on one side of anode 330 and a second cathode stack including cathodes 220C, 220D is located on the opposite side of anode 330. Each cathode stack is only adjacent to one anode, whereas anode 330 is adjacent to and between both of the cathode stacks in electrochemical cell 800.

Electrochemical cell 800 further includes separator layers 294, 296 positioned between adjacent cathodes 220 and anode 330. Each separator layer 294, 296 is a permeable membrane that functions to keep cathodes 220 and anode 330 physically separated to prevent an electrical short circuit. In different examples, separator layers 294, 296 may be formed from different materials or from substantially similar materials. The use of the two separator layers 294, 296, i.e., a 2-ply separator, allows further customization of electrochemical cell 800, e.g., to meet desired performance characteristics, as compared to an electrochemical cell with single-ply separator layers. As one example, each separator layer 294, 296 may be a polymer separator. In the example of electrochemical cell 800, anode 330 is covered by separator layers 294, 296. In other examples, separator layer 294, 296 may only be placed between adjacent cathodes and anodes or may cover one or more of cathodes 220.

Figure 13:
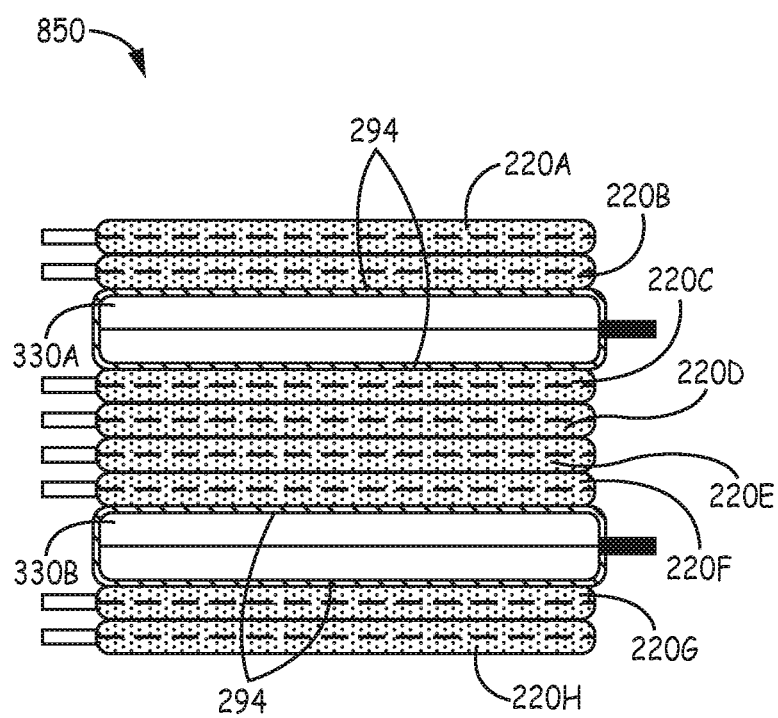

FIG. 13 illustrates electrochemical cell 850, which provides another example of an electrochemical cell configured such that cathodes stacks are outside of the anodes. Electrochemical cell 850 includes cathodes 220A, 220B, 220C, 220D, 220E, 220F, 220G, 220H and anodes 330A, 330B. Electrochemical cell 850 comprises a first cathode stack including cathodes 220A, 220B located on one side of anode 330A and a second cathode stack including cathodes 220C, 220D, 220E, 220F is located on the opposite side of anode 330A. The second cathode stack including cathodes 220C, 220D, 220E, 220F is also adjacent to anode 330B such that the second cathode stack is between anodes 330A, 330B. Electrochemical cell 850 further comprises a third cathode stack including cathodes 220G, 220H. The third cathode stack is adjacent to anode 330B such that anode 330B is between the third cathode stack and the second cathode stack within electrochemical cell 850.

Electrochemical cell 850 further includes separator 294 positioned between adjacent cathodes 220 and anodes 330. In the example of electrochemical cell 850, anodes 330 are covered by separator layer 294. In other examples, separator 294 may only be placed between adjacent cathodes and anodes or may cover one or more of cathodes 220.

Figure 14:
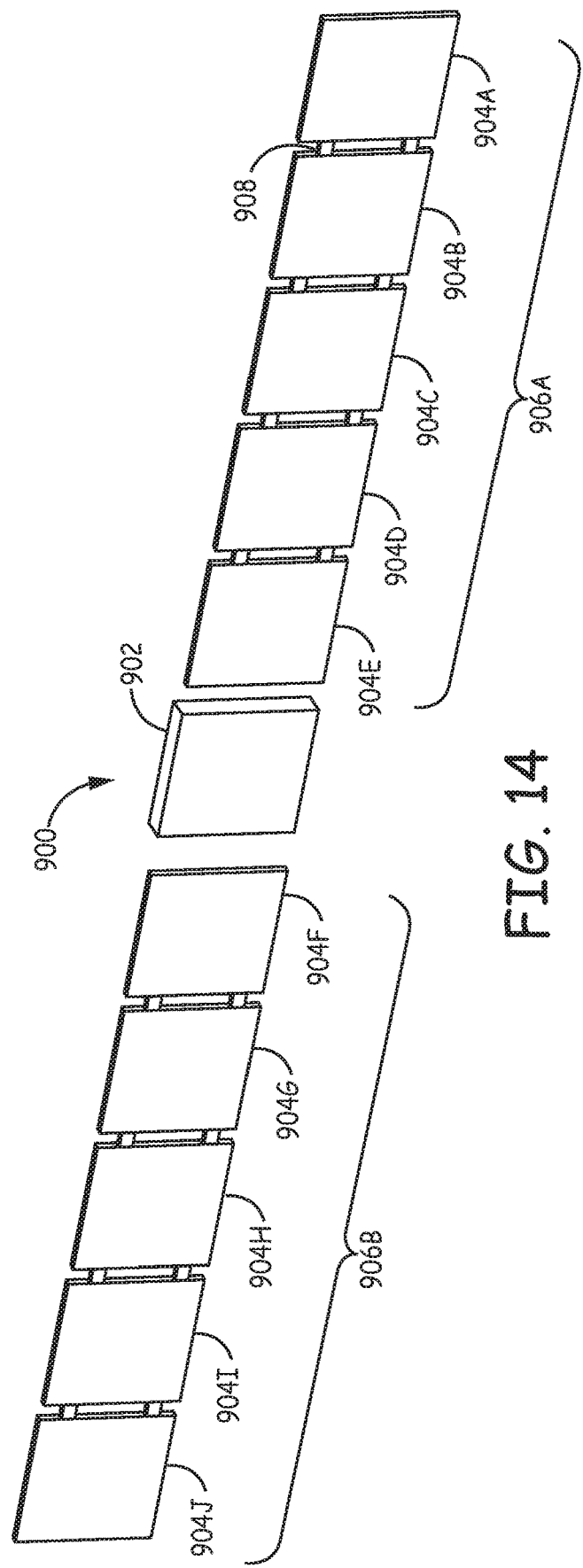
FIGS. 14 and 15 illustrate another example of an electrochemical cell with adjacent cathodes.

FIG. 14 illustrates an exploded view of another embodiment of an electrochemical cell 900. Electrochemical cell comprises anode 902 and cathodes 904A-904J. Cathodes 904A-904E and 904F-904J are connected together via current collector connectors 908 to form first cathode stack 906A and second cathode stack 906B.

Figure 15:
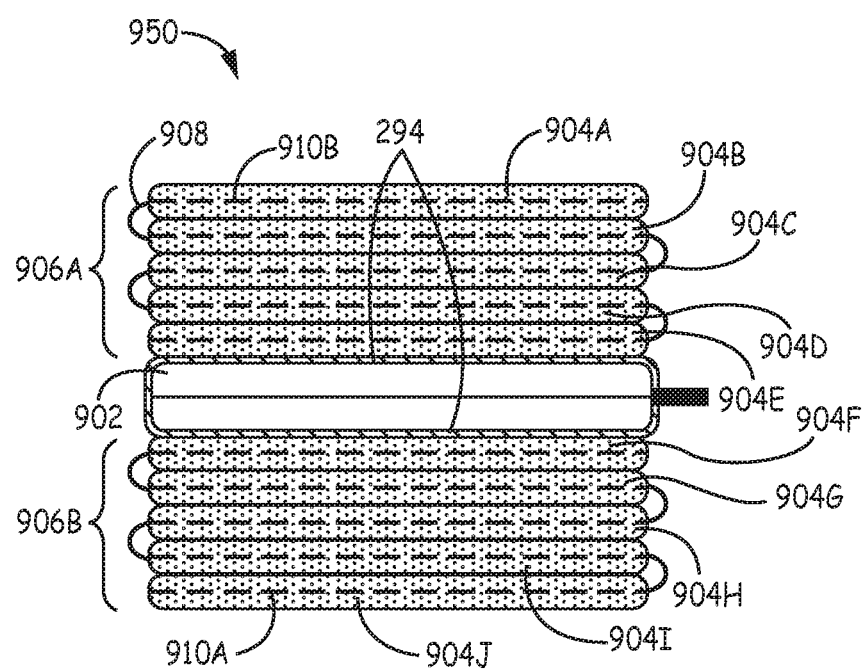

FIG. 15 illustrates electrochemical cell 950 having first cathode stack 906A located on one side of anode 902 and second cathode stack 906B located on the opposite side of anode 902. The cathode stacks are separated from the anode by separator layers 294 which fully cover the anode in this embodiment. The cathodes in each of the cathode stacks are connected together via current collector connectors 908. The current collector connectors 908 are exposed portions of a continuous current collector 910A and 910B which are not covered with cathode material.

Figure 16:
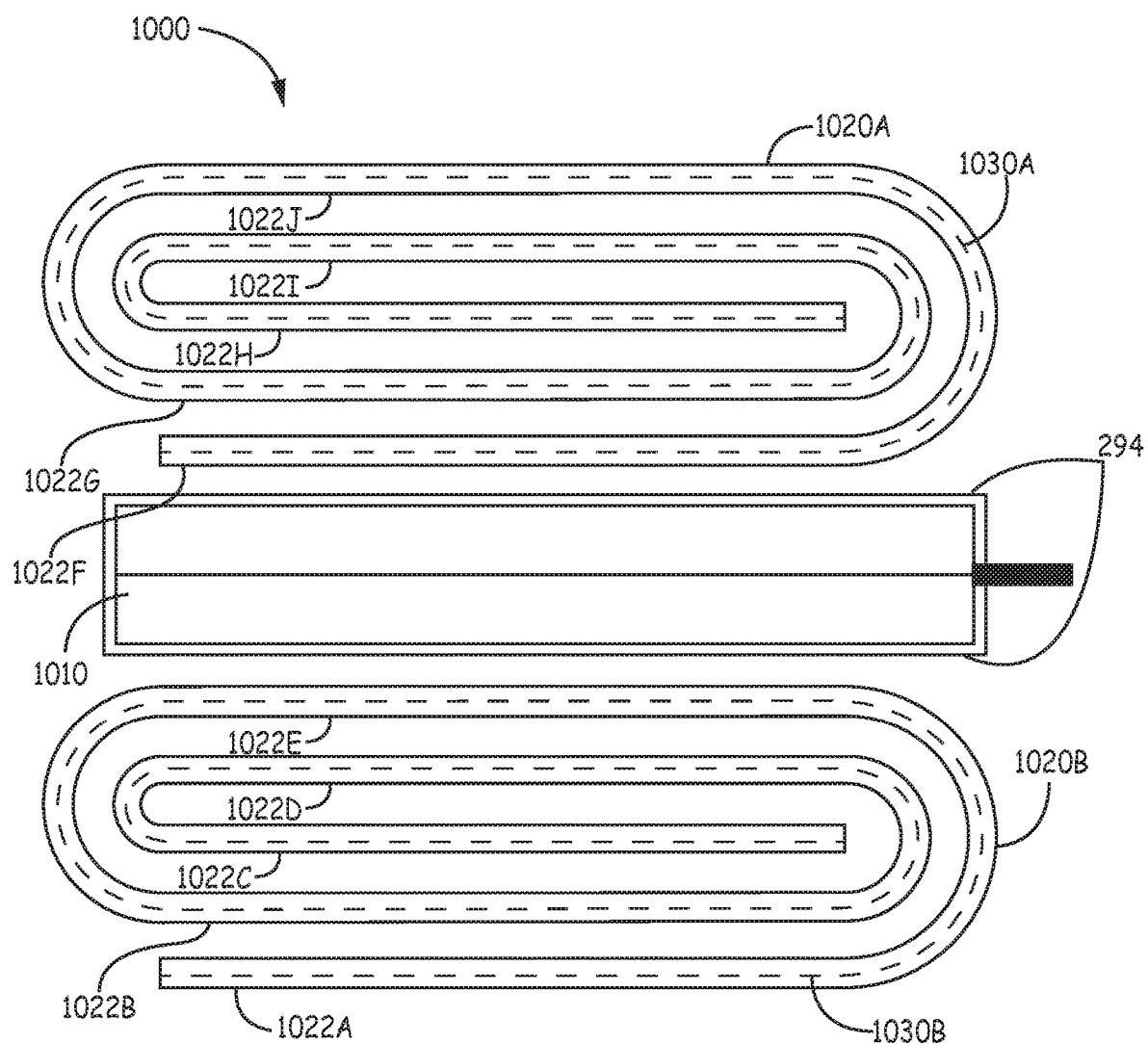
FIGS. 16 and 17 illustrate another example of an electrochemical cell with adjacent cathodes.
Figure 17:
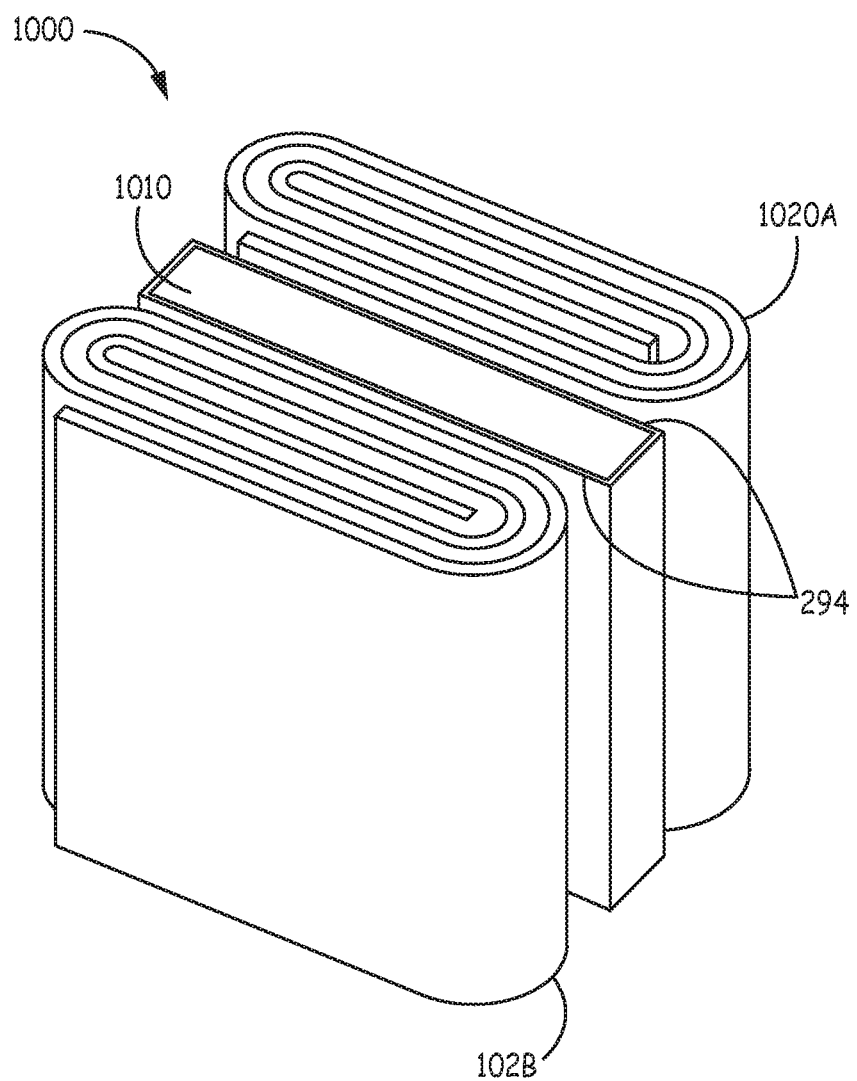

FIGS. 16 and 17 illustrate another embodiment of an electrochemical cell 1000 in cross-sectional and perspective views. Electrochemical cell 1000 comprises anode 1010 and cathode stacks 1020A and 1020B adjacent to the anode with separator layers 294 positioned between the anode and the adjacent cathode stacks. In this embodiment, cathode stacks 1020A and 1020B are shaped in the form of an oval-shaped coil wherein a continuous length of cathode material is folded into a stack substantially in the shape of a coil. In this embodiment, each cathode stack 1020 A and 1020B has cathodes in a stack in the form of cathode layers 1022F-1022J and 1022A-1022E, respectively. Cathode stacks 1020 A and 1020B contain current collector(s) 1030A and 1030B.

Various examples of this disclosure have been described. However, various modifications to the described examples can be made within the spirit of this disclosure. For example, while the disclosed energy storage techniques were generally described with respect to implantable medical devices in general and cardiac stimulators in particular, the disclosed energy storage techniques may be utilized in other applications including, for example, other implantable medical devices, such as implantable pumps, neurostimulators or other IMDs. In addition, the disclosed energy storage techniques may also be applied outside the medical field. For example, the disclosed energy storage techniques may be used in portable consumer electronics or other areas that utilize electrochemical cells. These and other examples are within the scope of the following claims.

What is claimed is:

1. An electrochemical cell comprising:
   a first cathode, wherein the first cathode includes a first current collector having first and second sides and a first cathode form of active material covering the first and second sides of the first current collector;
   a second cathode, wherein the second cathode includes a second current collector having first and second sides and a second cathode form of active material covering the first and second sides of the second current collector, wherein the first and second current collectors are each a single layer metallic plate or metallic foil, and
   wherein the first and second cathodes are adjacent one another in a stacked arrangement to form a cathode stack in the electrochemical cell;
   an anode adjacent to the cathode stack; and
   a separator surrounding all sides of the cathode stack, allowing for an electrical connection between the first and second cathode current collectors.

2. The electrochemical cell of claim 1, wherein the anode is a first anode and the separator is a first separator, the electrochemical cell further comprising:
   a second anode adjacent to the cathode stack and opposite the first anode relative to the cathode stack.

3. The electrochemical cell of claim 2,
   wherein the cathode stack further includes a third cathode such that the third cathode is adjacent the second cathode in the cathode stack, wherein the third current collector is a single layer metallic plate or metallic foil, and
   wherein the third cathode includes a third current collector and a third cathode form of active material covering the third current collector,
   wherein the third current collector is electrically connected with the first and second current collector, and
   wherein the separator surrounds all sides of the cathode stack, allowing for an electrical connection between the first, second and third cathode current collectors.

4. The electrochemical cell of claim 1, wherein the first cathode has a different active material than the second cathode such that the second cathode has a higher energy density than the first cathode.

5. The electrochemical cell of claim 1, wherein the second cathode is thicker than the first cathode as measured in a direction about parallel to the thickness of the cathode stack such that the second cathode has a higher energy density than the first cathode.

6. The electrochemical cell of claim 1, wherein the first cathode is similar to the second cathode.

7. The electrochemical cell of claim 1,
   wherein the first cathode includes a first electrically conductive tab extending from the first current collector,
   wherein the second cathode includes a second electrically conductive tab extending from the second current collector,
   wherein the first electrically conductive tab is electrically connected with the second electrically conductive tab.

8. A battery comprising
   a first cathode, wherein the first cathode includes a first current collector having first and second sides and a first cathode form of active material covering the first and second sides of the first current collector;
   a second cathode, wherein the second cathode includes a second current collector having first and second sides and a second cathode form of active material covering the first and seconds sides of the second current collector, wherein the first and second current collectors are each a single layer metallic plate or metallic foil, and
   wherein the first and second cathodes are adjacent one another in a stacked arrangement to form a cathode stack in the battery;
   an anode adjacent to the cathode stack;
   a separator surrounding all sides of the cathode stack, allowing for an electrical connection between the first and second cathode current collectors;
   electrolyte; and
   a battery housing that holds the cathode stack, the anode, the separator, and the electrolyte.

9. The battery of claim 8, wherein the anode is a first anode and the separator is a first separator, the battery further comprising:
   a second anode adjacent to the cathode stack and opposite the first anode relative to the cathode stack.

10. The battery of claim 9,
    wherein the first cathode is adjacent to the first anode,
    wherein the second cathode is adjacent to the second anode,
    wherein the first anode is longer than the second anode as measured in a direction about perpendicular to the thickness of the cathode stack,
    wherein the first cathode is longer than the second cathode as measured in the direction about perpendicular to the thickness of the cathode stack,
    wherein a thickness of the battery housing as measured in the direction about perpendicular to the thickness of the cathode stack varies to conform to the different lengths of the first anode and the second anode and the different lengths of the first cathode and the second cathode.

11. The battery of claim 8, wherein the first cathode has a substantially different active material than the second cathode such that the second cathode has a higher energy density than the first cathode.

12. The battery of claim 8, wherein the second cathode is thicker than the first cathode as measured in a direction about parallel to the thickness of the cathode stack such that the second cathode has a higher energy density than the first cathode.

13. The battery of claim 8, wherein the first cathode is similar to the second cathode.

14. A method of manufacture comprising:
positioning a first cathode and a second cathode adjacent one another in a stacked arrangement to form a cathode stack,
wherein the first cathode includes a first current collector having first and second sides and a first cathode form of active material covering the first and second sides of the first current collector,
wherein the second cathode includes a second current collector having first and second sides and a second cathode form of active material covering the first and second sides of the second current collector wherein the first and second current collectors are each a single layer metallic plate or metallic foil;
surrounding all sides of the cathode stack with a separator, allowing for an electrical connection between the first and second cathode current collectors, forming a separator-encapsulated cathode stack;
positioning an anode adjacent to the separator-encapsulated cathode stack; and
electrically connecting the first current collector and the second current collector.

15. The method of claim 14, further comprising:
locating, the anode and the separator-encapsulated cathode stack within a battery housing with the anode adjacent to the cathode stack; and
filling the battery housing with electrolyte.

16. The method of claim 15, further comprising electrically connecting the first current collector and the second current collector to a feedthrough pin that extends through the battery housing to form a positive battery terminal.

17. The method of claim 16, wherein the battery housing is electrically connected to the anode such that the battery housing serves as a negative battery terminal.

18. An implantable medical device comprising:
a hermetically sealed housing; and
a battery disposed within the housing for powering the implantable medical device, the battery comprising:
a first cathode, wherein the first cathode includes a first current collector having first and second sides and a first cathode form of active material covering the first and seconds sides of the first current collector;
a second cathode, wherein the second cathode includes a second current collector having first and second sides and a second cathode form of active material covering the first and second sides of the second current collector, wherein the first and second current collectors are each a single layer metallic plate or metallic foil, and
wherein the first and second cathodes are adjacent one another in a stacked arrangement to form a cathode stack in the battery;
an anode adjacent to the cathode stack;
a separator surrounding all sides of the cathode stack, allowing for an electrical connection between the first and second cathode current collectors;
and
a battery housing that holds the cathode stack, the anode, the separator, and the electrolyte.

19. The implantable medical device of claim 18, further comprising a control module within the hermetically sealed housing, wherein the control module controls electrical stimulation functions of the implantable medical device.

20. The implantable medical device of claim 19, wherein the implantable medical device is a cardiac stimulator.

* * * * *